United States Patent [19]

Reich

[11] 4,128,730

[45] Dec. 5, 1978

[54] CATALYTIC SPLITTING OF FORMIC ACID ESTERS ON HYDROGENATION CATALYSTS

[75] Inventor: Manfred Reich, Marl, Fed. Rep. of Germany

[73] Assignee: Chemische Werke Hüels Aktiengesellschaft, Marl, Fed. Rep. of Germany

[21] Appl. No.: 759,802

[22] Filed: Jan. 14, 1977

Related U.S. Application Data

[63] Continuation of Ser. No. 281,986, Aug. 18, 1972, abandoned, which is a continuation of Ser. No. 867,914, Oct. 20, 1969, abandoned.

[30] Foreign Application Priority Data

Oct. 26, 1968 [DE] Fed. Rep. of Germany ....... 1805403

[51] Int. Cl.$^2$ ............................................ C07C 29/24
[52] U.S. Cl. .................... 568/914; 252/459; 252/476; 568/885
[58] Field of Search ........... 260/643 B, 643 F, 638 A; 568/914, 885

[56] References Cited

U.S. PATENT DOCUMENTS

| 3,197,418 | 7/1965 | Maebashi et al. | 260/638 A |
| 3,384,659 | 5/1968 | Bate | 260/643 F |
| 3,462,500 | 8/1969 | Tummes et al. | 260/643 F |

FOREIGN PATENT DOCUMENTS

| 369574 | 1/1919 | Fed. Rep. of Germany | 260/638 A |
| 125946 | 3/1920 | United Kingdom | 260/638 A |
| 278777 | 10/1927 | United Kingdom | 260/643 B |

*Primary Examiner*—Joseph E. Evans
*Attorney, Agent, or Firm*—Gilbert L. Wells

[57] ABSTRACT

The amount of formic acid ester produced by the Oxo Process is reduced and the amount of alcohol is increased when the reaction product of said process, in contact with a copper/nickel supported catalyst, is subjected to elevated temperatures. Such catalysts are also useful for the conversion, by hydrogenation, of formyl esters to their corresponding alcohols.

21 Claims, No Drawings

CATALYTIC SPLITTING OF FORMIC ACID ESTERS ON HYDROGENATION CATALYSTS

CROSS-REFERENCE TO RELATED APPLICATION

This is a continuation of application Ser. No. 281,986, filed Aug. 18, 1972, abandoned which in turn is a continuation of application Ser. No. 867,914 filed Oct. 20, 1969 abandoned.

Applicant claims priority under 35 U.S.C. 119 for Application P 18 05 403.0, filed Oct. 26, 1968 in the Patent Office of the Federal Republic of Germany.

BACKGROUND OF THE INVENTION

The Oxo Process or Oxo-Synthesis is a well-established reaction of commercial import. (See: KirkOthmer, "Encyclopedia of Chemical Technology", 2nd Edition, Vol. 14, 373–390 [1967]; The Merck Index, 8th Ed., page 1197 [1968]; U.S. Pat. No. 3,462,500 of Tummes et al; and citations therein.). It is used in the industrial manufacture of aldehydes and alcohols from olefins, carbon monoxide and hydrogen. Unfortunately, undesirable formic acid esters of the corresponding alcohols are concurrently obtained to a considerable extent as unwanted by-products.

The formation of the esters reduces the yield of the more valuable aldehydes and alcohols. Furthermore, it is difficult to separate the esters by distillation from the reaction product. Finding a way to convert the formic acid esters into corresponding alcohols or aldehydes (if possible, without any large expenditure and without loss) is thus a most desirous goal.

These esters are conventionally saponified with acids or alkalis; mineral acids or Lewis acids (DAS [German Published Applications] 1,108,195 and 1,148,221) or alkaline-reacting substances (DAS 1,085,513) are used. However, such saponification leads to corrosion problems, particularly when acids are employed. Moreover, larger losses in yield are incurred when aldehydes are still present; the latter are difficult to separate from the alcohol mixture.

Saponification with mild alkali at elevated temperature, whereby decomposition to alcohol and gaseous products ($CO_2$, $H_2$, CO) takes place (DAS 1,258,855), is also undesirable because of the high pressures and temperatures required, especially since the alkali salt and the water of condensation must be constantly replenished during continuous operation.

In contrast thereto, cleaving hydrogenation of the formic acid esters is desirable, since a hydrogenation step is necessary in the production of alcohols, particularly according to the Oxo Process, in order to remove the hydrogenatable compounds, such as aldehydes and compounds with double bonds. For this purpose, conventional nickel catalysts are available. However, DAS 1,258,855, col. 4, advises against such a mode of operation, particularly because the high nickel consumption, resulting from unavoidable catalyst poisoning caused by the carbon monoxide, makes this process uneconomical.

H. Adkins reported ("Organic Reactions", 8, 1–27 [1954]) on the hydrogenation of esters to alcohols with only copper chromium catalysts, zinc chromium catalysts or Raney nickel catalysts. The more advantageous use of the catalysts of the subject invention in conjunction with formic acid esters, which was not reported by Adkins, could not be derived from the cited article.

SUMMARY OF THE INVENTION

The catalytic production of alcohols and aldehydes from olefins and carbon monoxide (with or without hydrogen) is enhanced and the amount of formic acid esters in the reaction product is reduced by subjecting the reaction product to elevated temperatures in contact with a supported mixed catalyst containing both copper and nickel. The same catalyst is useful for converting formic acid esters to their corresponding alcohols and/or aldehydes.

The catalyst may advantageously, but not necessarily, be modified by modifying additives which are conventional admixtures for copper hydrogenation catalysts. The employment of a support material having a rather large internal surface area, e.g. a surface area in excess of 20 square meters per gram, makes possible a reduction in reaction temperature without a concomitant sacrifice in yield. Incorporating a small amount (up to about one percent by weight) of alkaline material in the finished supported catalyst permits regeneration of the catalyst (by roasting and subsequent reduction with hydrogen) without the subsequent occurrence of considerable amounts of by-products therefrom.

An object of this invention is to convert to the corresponding alcohol formic acid ester produced in the preparation of alcohols and aldehydes from olefins and carbon monoxide. A further object is to split formic acid esters to respective alcohols in an economical fashion. A still further object is to effect such split with catalysts which are operative over longer periods of time with as high a conversion as possible and without appreciable (if any) loss in yield. Another object is to find a catalyst which will not be poisoned, or will be minimally poisoned, by contact with carbon monoxide at elevated reaction temperature. Still further objects are apparent from the following description.

DESCRIPTION OF THE INVENTION

Copper/nickel mixed catalysts are employed to reduce or eliminate formic acid esters produced in the reaction of olefins with carbon monoxide to form alcohols and aldehydes. These mixed catalysts are also useful in converting formic acid esters to their corresponding alcohols.

Suitably, the catalysts are introduced into reactors in the form of a solid bed through which a crude mixture containing at least one formic acid ester is passed, preferably in an at least partially vaporous phase, together with hydrogen at temperatures of between 120° and 250° C. and at any desired pressure, particularly between 0 and 350 atmospheres gauge.

In order to convert formic acid esters into alcohols on hydrogenation catalysts, the presence of hydrogen per se is not actually required, since the reaction takes place predominantly in accordance with the following equation:

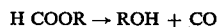

However, since hydrogenation catalysts have a dehydrogenating effect, in the absence of hydrogen a substantial amount of the respective aldehyde can be produced from the alcohol which is forming or already present, depending on the temperature conditions. The presence of hydrogen is additionally advantageous when, as is generally the case, the charged mixture contains aldehydes or other hydrogenatable compounds which must be removed by hydrogenation.

Depending on the partial hydrogen pressure and the temperature conditions, a part of the thus-formed carbon monoxide is hydrogenated to methane. If the hydrogen remaining after having been passed over the catalyst bed and after the hydrogenation product has been removed by condensation is reintroduced upstream of the catalyst bed, together with freshly charged product and fresh hydrogen, as is generally customary, for economy, then the carbon monoxide in the gaseous mixture must be eliminated from the cycle gas mixture by an appropriate amount of waste gas, so that the carbon monoxide level in the hydrogenation gas mixture does not become so high that the hydrogenating property of the catalyst is essentially affected. However, should this situation occur when the charge contains higher amounts of aldehydes, the hydrogenation of the aldehydes may be satisfactorily terminated in a second hydrogenating stage, i.e. after the larger part of the thus-formed carbon monoxide has been removed in a first stage.

Of particular advantage is the ability of the catalysts of this invention to operate even at low operating pressure.

The mixed catalysts are generally conventionally prepared by (a) applying to support material appropriate amounts of metal, i.e. copper and nickel, salts (with optional additives) in an aqueous solution' (b) drying; and if necessary, (c) decomposing the salts to the metals by heating and subsequent reduction, preferably in a hydrogen stream.

The mixed catalysts must contain at least 1 percent, preferably at least 3 percent, and ordinarily at most 90 percent by weight of copper and nickel, calculated as the sum of the weights of these elements and based upon the entire weight of the supported catalyst. The weight ratio of copper:nickel (based on respective elemental weights) can be varied, e.g., from 10:90 to 99:1 and is preferably between 40:60 and 90:10.

Based on the entire supported catalyst, the proportion thereof which is support material is usually from 10 to 99 percent by weight, preferably from 50 to 97 percent by weight. Any material which is useful as a catalyst support can be employed as the support material in the supported catalysts of this invention. Illustrative support materials are silica gel, kieselguhr, sintered silicic acid, aluminum oxide, calcined aluminum oxide, bauxite, kaolin, meerschaum and pumice. The preferred support materials are those based on silicic acid and aluminum oxide.

The splitting of formic acid esters to their respective alcohols is enhanced by employing support materials having a rather large internal surface, e.g. in excess of 20 square meters per gram. Silica gel and aluminum oxide are particularly good in this regard. (There is no critical upper limit to the surface area of the support as long as the material is capable of performing its function as a support. The internal surface can be, e.g. 200 or even 500 m$^2$/g). By employing support material with such large internal surface, the catalytic process can be conducted at a lower temperature than would otherwise be possible.

When the support has an internal surface of more than 20 square meters/gram, it is particularly advantageous for the finished supported catalyst to contain from about 0.1 to about 1.0 percent by weight of alkali metal, e.g. sodium and potassium, or alkaline earth metal, e.g. calcium and magnesium, calculated as the metal and based on the total weight of the supported catalyst. By providing this additive, the formation of by-products, such as hydrocarbons, in particular, which occurs in some cases, especially at elevated temperatures, is materially reduced or virtually completely eliminated. Furthermore, the resulting catalysts are resistant to high temperature treatment, such as catalyst regeneration, which is customarily effected by roasting with air at from 300° to 400° C. and subsequently reducing with hydrogen; the use of catalysts that do not contain alkali or alkaline earth metals often results in the production of considerable amounts of by-products during reactions following such treatment.

Although it is not essential that the catalysts contain modifying additives, such additives have a beneficial effect. They serve to extend the working life-of the catalysts; to raise the hydrogenation activity, and to lower the formation of by-products.

Suitable modifying additives are admixtures conventional for copper hydrogenation catalysts. They are applied to the catalyst support after or, more advantageously, together with the heavy metal compounds, i.e. compounds of copper and nickel. Illustrative modifying additives are, in particular, chromium or chromium-compounds introduced, for example, in the form of chromic acid; magnesium compounds applied, for instance, as magnesium nitrate or magnesium acetate; or phosphates employed, for example, as disodium ammonium phosphate or disodium hydrogen phosphate; tungstates, e.g. ammonium tungstate or sodium tungstate. or molybdates, e.g. ammonium molybdate, are likewise usable. These modifiers are generally employed in amounts of from 0.1 to 40 percent, preferably 0.5 to 10 percent by weight, based on the weight of copper and nickel. In the case of chromium or compounds thereof, the quantities are, in general, from 0.1 to 60 percent, preferably 1 to 20 percent by weight, based on the weight of copper and nickel and calculated as chromium.

Preferred examples of the overall combination of support material, copper, nickel and additives are, with proportions given in parts by weight, wherein the support material (kieselguhr, silica gel, aluminum oxide) contains the oxygen which may be combined chemically with the metals, whereas the metals are listed in the elemental form:

Kieselguhr 91.6,
Copper 4,
Nickel 4,
Chromium 0.4;
Silica Gel 87.3,
Copper 9.2,
Nickel 2.8,
Chromium 0.4,
Potassium 0.3;
Aluminum Oxide 92.0,
Copper 5.3,
Nickel 2.4,
Sodium 0.3;
Aluminum Oxide 88.0,
Copper 12.0,
Nickel 2.2,
Magnesium 3.6,
Sodium 0.2;
Silica Gel 87.9,
Copper 9.8,
Nickel 11.2, Phosphor 0.4,
Sodium 0.7;
Silica Gel 80.6,
Copper 14.0,
Nickel 2.5,
Chromium 2.0,
Calcium 0.6,
Potassium 0.3.

The formic acid esters which are advantageously converted to their corresponding alcohols at elevated temperatures with the subject catalysts are those of a great variety of alcohols. Said catalysts are particularly effective in the conversion of formic acid esters of normal lower 1-alkanols having from 1 to 8 carbon atoms, e.g. methanol, ethanol, propanol, butanol, pentanol, hexanol, heptanol and octanol. Liquid formic acid esters of alkanols having more than 8 carbon atoms, e.g. normal 1-nonanol, are also readily converted to the corresponding alkanol with these catalysts. The process is also applicable to formic acid esters of (a) isomers of the aforesaid alkanols, e.g. 2-butanol, 2-methyl-1-propanol, 2-ethyl-1-hexanol and isopropanol, of (b) corresponding polyols, including such diols as 2,3-butylene glycol, ethylene glycol and 2-ethyl-1,3-hexanediol, of (c) cycloaliphatic alcohols, e.g. cyclohexanol, methyl cyclopentanol and methyl cyclohexanol, and of d) unsaturated alcohols, e.g. allyl alcohol, crotyl alcohol and 2-ethyl-hexenol-1, which are converted by the hydrogenation into the corresponding saturated alcohols (propanol, n-butanol, 2-ethyl-hexanol-1).

The formic acid esters, either individually or in the form of mixtures with one another and/or in admixture with one or more alcohols and/or aldehydes, are readily converted to their corresponding alcohols according to the instant process, which is particularly applicable to admixtures obtained while working up reaction products of the oxo synthesis.

Without further elaboration, it is believed that one skilled in the art can, using the preceding description, utilize the present invention to its fullest extent.

EXAMPLE 1

In order to demonstrate the superiority of copper nickel mixed catalysts are compared to pure copper or nickel catalysts in the splitting of formic acid esters to alcohols, the corresponding supported catalysts are compared with one another with respect to their function. The support material is sintered kieselguhr in fragments of a diameter of about 3 to 8 millimeters (mm), since kieselguhr exhibits a relatively inert behavior. The salts are applied on this kieselguhr in a conventional manner from appropriate aqueous-ammoniacal solutions of basic copper carbonate, chromic acid and/or nickel formate; the masses thus produced are dried and reduced in a hydrogen stream, so that the finished supported catalysts exhibit the following contents of substances effective in the splitting reaction, calculated as metals in percent by weight and based on the total weight of the supported catalyst:

Catalyst A: 8% by weight of nickel
Catalyst B: 8% by weight of copper, 0.4% by weight of chromium
Catalyst C: 4% by weight of copper, 4% by weight of nickel, 0.4% by weight of chromium For purposes of additional comparison, a supported palladium catalyst is employed, produced in a corresponding fashion, by applying aqueous hydrochloric palladium chloride solution to the sintered kieselguhr, so that the finished catalyst contains 0.1 percent by weight of palladium (catalyst D). This amount is selected because palladium exhibits a considerably higher hydrogenating effect, and because the price of the palladium catalyst, for reasons of economy, is in the same order of magnitude as that of the remaining catalysts.

(a) Experimental Procedure:

60 grams per hour of 2-ethylhexyl formate is vaporized in a hydrogen cycle gas stream of 900 liters per hour at normal conditions and passed over 1 liter (bulk volume) of the respective catalyst disposed in a heatable pipe. The operating pressure is about 0.1 atmosphere gauge. After passing over the catalyst, the product is obtained by condensation, and such an amount of waste gas is removed from the cycle gas system that the carbon monoxide level in the cycle gas does not rise above about 10 percent by volume.

In the following Table, the contents are set forth, in percent by weight, of unreacted ester (2-ethylhexyl formate), aldehyde (2-ethylhexanal) produced, and alcohol (2-ethylhexanol) produced in the reaction product.

| Catalyst Temperature | 200° C | | | 220° C | | |
|---|---|---|---|---|---|---|
| | Ester | Aldehyde | Alcohol | Ester | Aldehyde | Alcohol |
| Catalyst A | 78 | 7 | 12 | 32 | 16 | 48 |
| Catalyst B | 78 | 1 | 18 | 38 | 4 | 54 |
| Catalyst C | 11 | 8 | 78 | 0.3 | 4 | 92 |
| Catalyst D | 79 | 1 | 17 | 65 | 2 | 30 |

The superiority of the copper nickel mixed catalyst C of this invention is clearly apparent.

(b) The same experiments are repeated, but in this case nitrogen is circulated in the cycle in place of a hydrogen cycle gas stream. Accordingly, the following values are obtained (in percent by weight of the product removed from the reactor):

| Catalyst temperature | 200° C | | | 220° C | | |
|---|---|---|---|---|---|---|
| | Ester | Aldehyde | Alcohol | Ester | Aldehyde | Alcohol |
| Catalyst A | 74 | 14 | 8 | 39 | 35 | 22 |
| Catalyst B | 85 | 5 | 7 | 73 | 15 | 9 |
| Catalyst C | 13 | 42 | 42 | 1.2 | 42 | 54 |
| Catalyst D | 85 | 2 | 10 | 75 | 5 | 16 |

Even in the non-hydrogenating splitting reaction, leading to aldehydes to a greater extent, in addition to alcohols, due to the dehydrogenating effect of the catalysts, the superiority of the copper nickel mixed catalyst C can clearly be seen.

EXAMPLE 2

A superior position is likewise occupied by copper nickel mixed catalyst applied to support materials having a large surface, whereby the hydrogenating efficiency and the splitting effect are additionally promoted so that the temperatures can be maintained at a lower level. This is shown by the following Example:

A nickel catalyst (Catalyst E) and a copper nickel mixed catalyst (Catalyst F) according to the invention, both disposed on silica gel having a surface of 200 m$^2$/g [determined in accordance with the BET method (a method for determining the surface area of an adsorbent, by Brunauer, Emmett, and Teller)] as the support material, are compared with each other.

Catalyst E contains 12 percent by weight of nickel in the reduced condition;

Catalyst F contains 9 percent by weight of copper and 3 percent by weight of nickel, based on the total weight, including the support.

The catalysts are produced in the usual manner by saturating the silica gel with the appropriate aqueous-ammoniacal metallic salt solutions, subsequent drying, and reduction in a hydrogen stream.

In correspondence with the conditions and the mode of operation of Example 1 (a) (hydrogen), ethylhexyl formate is decomposed on these catalysts; the following data are obtained (values are in percent by weight of the product removed from the reactor):

| | Catalyst Temperature 180° C | | | 200° C | | |
|---|---|---|---|---|---|---|
| | Ester | Aldehyde | Alcohol | Ester | Aldehyde | Alcohol |
| Catalyst E | 68 | 1.2 | 29 | 5 | 2.5 | 89 |
| Catalyst F | 8 | 1 | 89 | 0.5 | 2 | 95 |

In correspondence with the conditions and the mode of operation of Example 1(b) (nitrogen), the following values are obtained when decomposing ethylhexyl formate (percent by weight of the product removed from the reactor):

| | Catalyst Temperature 180° C | | | 200° C | | |
|---|---|---|---|---|---|---|
| | Ester | Aldehyde | Alcohol | Ester | Aldehyde | Alcohol |
| Catalyst E | 52 | 10 | 35 | 6 | 33 | 58 |
| Catalyst F | 8 | 24 | 65 | 0.5 | 30 | 66 |

EXAMPLE 3

Ethylhexyl formate is decomposed on a catalyst produced as Catalyst F of Example 2 and containing, per analysis, less than 0.05 percent by weight of alkalis and alkaline earth, calculated as metals and based on the total weight of the catalyst; this is done in accordance with the conditions and the mode of operation of Example 1(a) (hydrogen). The catalyst temperature is 220° C. In the reactor product, there is still 28 percent by weight of hydrocarbons (mainly ethylhexane and heptane), in addition to 0.1 percent by weight of ester (ethylhexyl formate), 6 percent by weight of aldehyde (ethylhexanal) and 62 percent by weight of alcohol (ethylhexanol).

In a second catalyst batch, NaOH is added during the preparation of the aqueous solution in such an amount that the finished catalyst contains 0.3 percent by weight of sodium. With the same mode of operation, the reactor product contains 0.1 percent by weight of ester, 7 percent by weight of aldehyde, and 88 percent by weight of alcohol; the hydrocarbon content has decreased to 3 percent by weight.

EXAMPLE 4

An amount of 1 liter of catalyst is filled into a tube, this catalyst containing 9.2 percent by weight of copper, 2.8 percent by weight of nickel, 0.4 percent by weight of chromium and 0.3 percent by weight of potassium on silica gel (surface 200 square meters/gram) as the support and having been produced by applying the appropriate amounts of salt (basic copper carbonate, nickel formate, chromic acid, potassium hydroxide) from an aqueous-ammoniacal solution, drying, and subsequent reduction in a hydrogen stream. At a temperature of 190° C. and an operating pressure of 0.1 atmosphere gauge, there is passed over the catalyst 150 grams/hour of a fraction, produced when working up products from an oxo synthesis, in the vaporized phase, together with 1000 liters/hour at normal conditions of hydrogen; this fraction (according to analysis by gas chromatography) contains, in addition to other compounds:

45.1% by weight of n-butanol
25.8% by weight of isobutanol
2.1% by weight of n-butyraldehyde
1.6% by weight of isobutyraldehyde
9.0% by weight of n-butyl formate
2.8% by weight of isobutyl formate Thereafter, a condensing step is conducted in a cooling system. The unconsumed hydrogen is reintroduced into the hydrogenation process as cycle gas; a small portion is removed from the cycle gas stream in the form of waste gas.

The condensed reactor product contains, in addition to other compounds:

55.4% by weight of n-butanol
30.2% by weight of isobutanol
0.2% by weight of n-butyraldehyde
0.1% by weight of isobutyraldehyde
0.06% by weight of n-butyl formate
0.03% by weight of isobutyl formate Thus, the formic acid esters have been converted into the corresponding alcohols almost completely, and the aldehydes have been hydrogenated to the corresponding alcohols to the larger part thereof.

EXAMPLE 5

This example is conducted as Example 4, with the difference that the hydrogenation is conducted at a temperature of 170° C. and a pressure of 15 atmospheres gauge. The condensed reactor product contains, in addition to other compounds:

55.5% by weight of n-butanol
30.3% by weight of isobutanol
0.1% by weight of n-butyraldehyde
0.05% by weight of isobutyraldehyde
0.02% by weight of n-butyl formate
0.01% by weight of isobutyl formate Consequently, the splitting and hydrogenation steps have taken place even somewhat more completely than in Example 4.

EXAMPLE 6

In accordance with Example 4, a mixture having the same composition as in that example is split in a hydrogenating manner at 180° C. and an operating pressure of 0.1 atmosphere gauge on a catalyst containing 5.3 percent by weight of copper, 2.4 percent by weight of nickel, and 0.3 percent by weight of sodium on aluminum oxide (surface 80 square meters/gram) as the support. The condensed reactor product contains, in addition to other compounds:

55.5% by weight of n-butanol
30.2% by weight of isobutanol
0.15% by weight of n-butyraldehyde
0.1% by weight of isobutyraldehyde
0.03% by weight of n-butyl formate
0.01% by weight of isobutyl formate

EXAMPLE 7

A hydrogenating splitting reaction is conducted in accordance with Example 6, with the difference that, in place of the mixture employed in Example 6, n-propyl formate is utilized in an amount of 60 grams/hour. The condensed reactor product comprises, in addition to 0.5 percent by weight of n-propyl formate and 0.4 percent by weight of propionaldehyde, predominatnly n-propanol.

EXAMPLE 8

A hydrogenating splitting reaction is carried out in accordance with Example 6, with the difference that, in place of the mixture employed in that example, n-heptyl formate is utilized in an amount of 60 grams/hour. The condensed reactor product consists, in addition to 0.8 percent by weight of n-heptyl formate and 0.5 percent by weight of n-heptanal, predominantly of n-heptanol.

Following the procedure of Example 8 and replacing the n-heptyl formate with an equivalent amount of either the formic acid ester of isobutanol or the formic acid diester of ethylene glycol produces predominantly the corresponding alcohol.

The preceding examples can be repeated with similar success by substituting the generically and specifically described reactants and operating conditions of this invention for those used in the preceding examples.

I claim:

1. In a process for reducing the amount of formic acid ester in an alkanolic admixture thereof prepared in the oxo synthesis, said formic acid ester consisting of a reaction product of said oxo synthesis, the improvement comprising:
a splitting said formic acid ester in a predominantly liquid state to predominantly the corresponding alcohol by introducing the formic acid ester into a reactor, hydrogenating the formic acid ester in contact with a supported catalytically effective metallic catalyst in a solid bed at a temperature of about 120° to 250° C. and a pressure of about 0 to 350 atmospheres gauge, said supported metallic catalyst consisting essentially of per 100 parts by weight, (a) from 10 to 99 parts by weight of support, and (b) from 90 to 1 part by weight of metallic catalyst calculated on the metal content, said metallic catalyst consisting essentially of a mixture of reduced copper and nickel salts in which the ratio of copper to nickel is from 10:90 to 99:1.

2. The process of claim 1, wherein the liquid formic acid ester is an alkyl formate.

3. In a process for reducing the amount of formic acid alkyl ester in an alkanolic admixture thereof prepared in the oxo synthesis, said formic acid alkyl ester consisting of a reaction product of said oxo synthesis, the improvement comprising:
splitting said formic acid alkyl ester to predominantly the corresponding alcohol by introducing the formic acid alkyl ester into a reactor, subjecting the ester in contact with a supported catalytically effective metallic catalyst in a solid bed, said supported metallic catalyst consisting essentially of, per 100 parts by weight, (a) from 10-99 parts by weight of support, and (b) from 90-1 part by weight of metallic catalyst calculated on the metal content, said metallic catalyst consisting essentially of a mixture of reduced copper and nickel salts in which the ratio of copper to nickel is from 10:90 to 99:1, to a temperature of from 120° to 250° C., and a pressure of 0 to 350 atmospheres gauge, the alkyl ester having from 1 to 9 carbon atoms.

4. In a process for reducing the amount of formic acid ester in an alkanolic admixture thereof prepared in the oxo synthesis, said formic acid ester consisting of a reaction product of said oxo synthesis, the improvement comprising:
preparing an alkanol from its corresponding formic acid ester by splitting the formic acid ester by introducing the formic acid ester into a reactor and subjecting the formic acid ester, at least partially in gaseous state to an elevated temperature of about 120° to 250° C. and a pressure of about 0 to 350 atmospheres gauge in contact with a supported catalytically effective metallic catalyst in a solid bed, said supported metallic catalyst consisting essentially of per 100 parts by weight (a) from 10 to 99 parts by weight of support, and (b) from 90 to 1 part by weight of metallic catalyst calculated on the metal content, said metallic catalyst consisting essentially of a mixture of reduced copper and nickel salts in which the ratio of copper to nickel is from 10:90 to 99:1.

5. The process of claim 4, wherein said elevated temperature is from 120° to 250° C.

6. The process of claim 1, further comprising from 0.1 to 1.0 percent by weight, based on the entire weight of the supported catalyst, of a member selected from the group consisting of reduced alkali metal and alkaline earth metal salts.

7. The process of claim 6, further comprising a modifying additive comprising from 0.1 to 40 percent by weight, based on the weight of said metal in said metallic catalyst, of a member selected from the group consisting of reduced magnesium, phosphorus, tungsten and molybdenum salts.

8. The process of claim 6, further comprising a modifying additive comprising from 0.1 to 60 percent by weight, based on the weight of said metal in said metallic catalyst, of a reduced chromium salt.

9. The process of claim 3, further comprising from 0.1 to 1.0 percent by weight, based on the entire weight of the supported catalyst, of a member selected from the group consisting of reduced alkali metal and alkaline earth metal salts.

10. The process of claim 9, further comprising a modifying additive comprising from 0.1 to 40 percent by weight, based on the weight of said metal in said metallic catalyst, of a member selected from the group consisting of reduced magnesium, phosphorus, tungsten and molybdenum salts.

11. The process of claim 9, further comprising a modifying additive comprising from 0.1 to 60 percent by weight, based on the weight of said metal in said metallic catalyst, of a reduced chromium salt.

12. The process of claim 4, further comprising from 0.1 to 1.0 percent by weight, based on the entire weight of the supported catalyst, of a member selected from the group consisting of reduced alkali metal and alkaline earth metal salts.

13. The process of claim 12, further comprising a modifying additive comprising from 0.1 to 40 percent by weight, based on the weight of said metal in said metallic catalyst, of a member selected from the group consisting of reduced magnesium, phosphorus, tungsten and molybdenum salts.

14. The process of claim 12, further comprising a modifying additive comprising from 0.1 to 60 percent by weight, based on the weight of said metal in said metallic catalyst, of a reduced chromium salt.

15. The process of claim 14, wherein said modifying additive comprises from 1 to 20 percent by weight.

16. The process of claim 1, wherein said ratio of copper to nickel is from 50:50 to 77:23.

17. The process of claim 3, wherein said ratio of copper to nickel is from 50:50 to 77:23.

18. The process of claim 4, wherein said ratio of copper to nickel is from 50:50 to 77:23.

19. The process of claim 1, wherein said formic acid ester is selected from the group consisting of n-butylformate, isobutylformate, ethylhexylformate, n-propylformate, n-heptylformate and mixtures thereof.

20. The process of claim 2, wherein said formic acid ester is selected from the group consisting of n-butylformate, isobutylformate, ethylhexylformate, n-propylformate, n-heptylformate and mixtures thereof.

21. The process of claim 4, wherein said formic acid ester is selected from the group consisting of n-butylformate, isobutylformate, ethylhexylformate, n-propylformate, n-heptylformate and mixtures thereof.

* * * * *